(12) United States Patent
Bell et al.

(10) Patent No.: US 9,127,136 B1
(45) Date of Patent: Sep. 8, 2015

(54) PURIFICATION OF MONOMER FROM RECYCLE POLYESTERS

(71) Applicant: SABIC Global Technologies B.V, Bergen op Zoom (BL)

(72) Inventors: Philip Wesley Bell, Mount Vernon, IN (US); Osit Karroonnirun, Mount Vernon, IN (US); Shankar Kollengodu Subramanian, Evansville, IN (US)

(73) Assignee: SABIC GLOBAL TECHNOLOGIES B.V. (NL)

( * ) Notice: Subject to any disclaimer, the term of this patent is extended or adjusted under 35 U.S.C. 154(b) by 0 days.

(21) Appl. No.: 14/335,197

(22) Filed: Jul. 18, 2014

(51) Int. Cl.
  *C08G 63/02* (2006.01)
  *C08J 11/24* (2006.01)
  *C08G 63/00* (2006.01)

(52) U.S. Cl.
  CPC ...... *C08J 11/24* (2013.01); *C08G 63/00* (2013.01)

(58) Field of Classification Search
  CPC .............................. C08G 63/78; C08G 67/04
  USPC ............... 210/143, 198.2, 656; 528/271, 272
  See application file for complete search history.

(56) References Cited

U.S. PATENT DOCUMENTS

| | | | |
|---|---|---|---|
| 6,444,854 B1 | 9/2002 | Dapremont et al. | |
| 6,812,458 B2 * | 11/2004 | Gregori et al. | 250/288 |
| 7,178,386 B1 * | 2/2007 | Gamble et al. | 73/61.57 |
| 7,261,812 B1 * | 8/2007 | Karp et al. | 210/198.2 |
| 2006/0074136 A1 | 4/2006 | Smith et al. | |
| 2006/0086667 A1 | 4/2006 | Hauck et al. | |
| 2007/0299150 A1 | 12/2007 | Nakao et al. | |

FOREIGN PATENT DOCUMENTS

| | | |
|---|---|---|
| JP | 2008088096 A | 4/2008 |
| JP | 2012149285 A | 8/2012 |

OTHER PUBLICATIONS

Riju Singhal, et al. Separation and liquid chromatography using a single carbon nanotube; Scientific Report: Article No. 510; Published Jul. 13, 2012.*

International Search Report for International Application No. PCT/US2015/015131, Application Filing Date—Feb. 10, 2015; Date of Mailing—May 14, 2015, 5 pages.

Written Opinion for International Application No. PCT/US2015/015131; Application Filing Date—Feb. 10, 2015; Date of Mailing—May 14, 2015, 7 pages.

* cited by examiner

*Primary Examiner* — Terressa Boykin
(74) *Attorney, Agent, or Firm* — Cantor Colburn LLP

(57) ABSTRACT

A method of recycling bis(hydroxyalkyl) terephthalate monomer from a composition comprising a terephthalate-containing polymer includes depolymerizing the terephthalate-containing polymer to provide the bis(hydroxyalkyl) terephthalate; and separating the bis(hydroxyalkyl) terephthalate from the composition comprising the depolymerized terephthalate-containing polymer by continuous multi-column liquid chromatography.

43 Claims, No Drawings

PURIFICATION OF MONOMER FROM RECYCLE POLYESTERS

BACKGROUND

Polyesters such as poly(ethylene terephthalate) (PET) have excellent thermal and mechanical properties. The main applications of PET include the manufacture of video and audio tapes, textiles, X-ray films, and food packaging, particularly for water and soft-drink bottles. In 2009, the world consumption of PET packaging alone was about 15.5 metric tons, and it has been estimated to increase to almost 19 metric tons by 2017, a 5.2% growth rate per year. Despite its many benefits, items made from PET have typically been used for a short period of time and then disposed of, especially water and soft-drink bottles.

Accumulation of the resulting waste from petroleum-based plastics such as PET has become an environmental concern worldwide. PET has been present in nature for only a comparatively short period of time, and microorganisms have not yet developed new enzyme structures to consume them. As a result, articles made from PET often end their life cycles either buried in landfill sites or burned, which can generate unwanted gaseous emissions. Therefore, other end of life solutions for PET, such as recycling, have been proposed.

One approach to recycling is based on the depolymerization of PET. Many processes for PET depolymerization have been studied, depending on the end use of the reclaimed products. Each process has its own advantages and disadvantages. A disadvantage of some methods is difficulty in separating the reclaimed products in a sufficiently pure state for further use. There accordingly remains a need in the art for improved methods for the recycling of PET based on depolymerization, particularly purifying depolymerization products.

SUMMARY OF THE INVENTION

Various illustrative embodiments are set forth herein, and are not to be viewed as limiting the scope of the claims.

A method of recycling a bis(2-hydroxyalkyl) terephthalate monomer from a terephthalate-containing polymer composition is disclosed, the method comprising: depolymerizing the terephthalate-containing polymer to provide bis(hydroxyalkyl) terephthalate; and separating the bis(hydroxyalkyl) terephthalate from the composition comprising the depolymerized terephthalate-containing polymer by continuous multi-column liquid chromatography.

In another embodiment, a method of recycling a polyester comprising ethylene terephthalate units comprises: depolymerizing the polyester in the presence of a $C_{1-6}$ alkylene diol and a alcoholysis catalyst to provide a composition comprising bis(hydroxyalkyl) terephthalate; and separating the bis (hydroxyalkyl) terephthalate from the depolymerized composition by continuous multi-column liquid chromatography, using a silica stationary phase and a mobile phase composition comprising a combination of solvents.

In another embodiment, a method of recycling a polyester comprising ethylene terephthalate units comprises: depolymerizing the polyester in the presence of ethylene glycol and a glycolysis catalyst to provide a composition comprising bis(2-hydroxyethyl) terephthalate; and separating the bis(2-hydroxyethyl) terephthalate from the depolymerized composition by continuous multi-column liquid chromatography, using a silica stationary phase and a mobile phase composition comprising a combination of solvents.

The invention is further illustrated and described by the following detailed description, examples, and claims.

DETAILED DESCRIPTION

The inventors hereof have discovered a surprisingly effective method for purifying a reclamation product of a terephthalate-containing polymer, in particular a bis(hydroxyalkyl) terephthalate, which can be obtained from the alcoholysis of poly(ethylene terephthalate).

The terephthalate-containing polymer can be obtained from any suitable source, which can include manufacturing overrun or scrap, or used consumable goods such as beverage bottles, food containers, other liquid containers, packaging, and/or synthetic fibers, films, and yarns. In preparation for the depolymerization of the polymer, the used consumable goods can be treated by one or more processes, including but not limited to: i) sorting, ii) pre-washing, iii) coarse cutting, iv) removal of stones, glass and metal, v) air sifting to remove film, paper and labels, vi) grinding, dry and/or wet, vii) removal of poly(vinyl chloride), high density poly(ethylene), low density poly(ethylene), and/or other polymers, viii) hot wash, ix) caustic wash, x) caustic surface etching, xi) rinsing, xii) clean water rinsing, xiii) drying, xiv) air sifting of flakes, and xv) flake sorting. The foregoing processes can be used singularly or in combination, in any desirable order to prepare terephthalate polyester for the depolymerization reaction.

The terephthalate-containing polymer can be in the form of a chip, flake, granule, powder, and/or other particle form that preferably does not become airborne dust in a manufacturing plant.

The terephthalate-containing polymer comprises terephthalate ester units, optionally in combination with other types of polymer units. The terephthalate-containing polymer is preferably a terephthalate-containing polyester, and most preferably a polyester comprising ethylene terephthalate repeat units. The terephthalate-containing polymer is not limited to a linear homopolymer. For example, a terephthalate-containing polymer can include branched, hyperbranched, dendritic, cyclic, and/or star-shaped architectures. The terephthalate-containing polymer can be a copolymer, for example, a random copolymer, block copolymer, multiblock copolymer, alternating copolymer, terpolymer, or the like. In an embodiment, the terephthalate-containing polymer is a PET homopolymer, or a polyester copolymer comprising ethylene terephthalate repeat units, for example a poly(ethylene terephthalate-co-butylene terephthalate) copolymer comprising ethylene terephthalate and butylene terephthalate repeat units.

The terephthalate-containing polymer can be part of a composition containing other polymers, for example poly (vinyl chloride). The other polymers (e.g., poly(vinyl chloride) can be present in an amount of 0 wt % to 5 wt %, or 0 wt % to 1 wt %, or 0 wt % to 0.1 wt %, or more preferably 0 wt % to 0.001 wt %, each based on a total weight of the terephthalate-containing polymer. The terephthalate-containing polymer can contain low density polyethylene (LDPE) and/or high density polyethylene (HDPE) in an amount of 0 wt % to 5 wt %, 0 wt % to 1 wt %, 0 wt % to 0.1 wt %, and more preferably in an amount of 0 wt % to 0.001 wt % based on a total weight of the terephthalate-containing polymer.

The composition comprising the terephthalate-containing polymer can further comprise additives, for example impact modifiers such as bulk acrylonitrile-butadiene-styrene (ABS), acrylonitrile-butadiene-styrene emulsions, styrene-acrylonitrile (SAN), or other thermoplastic or thermoset polymers, for example polycarbonate. However, the total amount of polymer other than the terephthalate-containing polymer is 0 wt % to 20 wt %, or 0 wt % to 10 wt %, or 0 wt % to 5 wt %, or more preferably 0 wt % to 1 wt %, each based on a total weight of the terephthalate-containing polymer.

In addition, the composition comprising the terephthalate-containing polymer can comprise other additives known for use in formulating the terephthalate-containing polymer, for example mold release agents, UV stabilizers, anti-drip agents, antioxidants, flame retardants, flame retardant synergists, heat stabilizers, quenchers, phosphate stabilizers, pigments, dyes, titanium dioxides, carbon blacks, talcs, glasses, calcium carbonate, and combinations thereof. However, in an embodiment, the total amount of all additives is 0 wt % to 20 wt %, or 0 wt % to 15 wt %, or 0 wt % to 10 wt %, or more preferably 0 wt % to 5 wt %, each based on a total weight of the terephthalate-containing polymer.

The composition comprising the terephthalate-containing polymers is depolymerized. Chemical recycling processes for terephthalate-containing polymers, in particular terephthalate-containing polyesters include alcoholysis (glycolysis in the case of a glycol), hydrolysis, methanolysis, aminolysis, and others. Alcoholysis (glycolysis in the case of a glycol) is preferred, and involves the insertion of the alkylene diol (or glycol) into the chains comprising the terephthalate units to yield bis(hydroxyalkyl)terephthalate.

The depolymerization reaction mixture comprises a $C_{1-5}$ alkylene diol comprising 2 to 5 carbons. The diol can be branched or non-branched. In a preferred embodiment, the diol is a linear diol such as 1,2-ethanediol (ethylene glycol), 1,3-propanediol, and 1,4-butanediol, and 1,5-pentanediol. In an embodiment, the diol is ethylene glycol (EG) and/or 1,4-butanediol (BD).

The diol can be present in the reaction mixture in an amount of about 1 to about 20 molar equivalents relative to the total moles of terephthalate repeat unit present in the terephthalate-containing polymer, more particularly about 4 to about 20 molar equivalents, about 4 to about 16 molar equivalents, about 6 to about 16 molar equivalents, or about 8 to about 16 molar equivalents. Additionally, the diol can be used in an amount less than 16 molar equivalents such as, for example, about 4 to about 12 molar equivalents, about 6 to about 12 molar equivalents, or about 8 to 12 molar equivalents relative to total moles of terephthalate repeat unit present in the terephthalate-containing polymer. In a preferred embodiment, the diol is present in an amount of about 1 to about 4 molar equivalents relative to total moles of terephthalate repeat unit present in the terephthalate-containing polymer, and the terephthalate reaction product contains terephthalate oligomers, for example in an amount of about 25 wt % based on a total weight of the terephthalate reaction product.

The catalysts used in the alcoholysis can be selected from those known organometallic compounds, particularly compounds of tin or titanium. Preferred catalysts include tetraalkyl titanates with the alkyl up to 8 carbon atoms such as tetrapropyl titanate (TPT). The quantity of catalyst is usually about 500 ppm titanium based on total weight.

The depolymerization of the terephthalate-containing polymer can be carried out in an inert atmosphere or in the air. The depolymerization can be conducted under pressure ranging from 0.01 to 1000 atmospheres (atm), preferably 0.1 to 100 atm, more preferably 1 atm. Although a solvent can be present, in a preferred embodiment, the depolymerization requires no additional solvent; that is, the diol also acts as the solvent.

The alcoholysis temperature is typically elevated, for example 200 to 300° C., for example 240° C. and 250° C. In a preferred embodiment, the glycols used in the alcoholysis are pre-treated by heating in order to drive off any moisture contained, if any, in them. Although this pretreatment is not necessary, it is of benefit since glycols usually absorb moisture and moisture can poison the catalyst used in the alcoholysis.

The depolymerization reaction mixture is typically, although not necessarily, agitated (e.g., stirred). The progress of the reaction can be monitored by standard techniques (e.g., nuclear magnetic resonance spectroscopy (NMR), gas phase chromatography (GPC), or high pressure liquid chromatography (HPLC)), although visual inspection is generally sufficient, insofar as a transparent reaction mixture indicates that the polymer has reacted to an extent sufficient to allow all solid material to dissolve.

The dihydroxy terephthalate diester can be present in the crude product in an amount of 50 wt % to 100 wt %, 90 wt % to 100 wt %, 94 wt % to 100 wt %, or more particularly 96 wt % to 100 wt %, based on the weight of the terephthalate reaction product. Preferably the dihydroxy terephthalate diester is bis(2-hydroxyethyl) terephthalate (BHET). The terephthalate oligomers can be present in the crude product in an amount of 0 wt % to 40 wt %, more particularly 5 wt % to 35 wt %, and even more particularly 10 wt % to 25 wt % based on the weight of terephthalate reaction product.

The separation of the dihydroxy terephthalate diester, for example BHET can be accomplished in stationary bed chromatography, but is not limited to stationary bed and can also be conducted in simulated moving bed chromatography. The liquid chromatography can be simulated moving bed chromatography, such that the feed composition forms a raffinate stream and an extract stream. Depending on the solvent-sorbent combination selected, the dihydroxy terephthalate diester can partition into either the extract or the raffinate stream.

The packing material used in the chromatography can be any packing material that enables the separation of dihydroxy terephthalate diester from the other components of the feed composition. Examples of suitable packing materials include natural polymer resins, such as agarose or dextran, inorganic resins, such as silica, or synthetic polymer resins, e.g. styrene-divinyl benzene. To these packing materials, conventional ligands are advantageously coupled, such as affinity ligands, ion exchange ligands, hydrophobic interaction chromatography (HIC) ligands, chelating ligands, thiophilic ligands, or multimodal ligands. In an embodiment, the inorganic particles are silica. In another embodiment, the stationary phase contains silica gel particles. Preferably the silica gel is a functionalized silica gel.

The method can be performed in any suitable system arrangement. In an embodiment, the method further comprises performing the chromatography in a stationary bed column. In another embodiment, the method further comprises performing the chromatography in a simulated moving-bed. Continuous multi-column chromatography processes include simulated moving bed (SMB) chromatography, partition, ion exchange, molecular exclusion, and affinity chromatography.

An industrial-scale simulated moving bed (SMB) unit can be used for the effective separation of dihydroxy terephthalate diester from a complex mixture of the alcoholysis products of waste PET. An industrial scale unit can include a controller to adjust the switching time and a frame that supports a rotation gear, a drive assembly, and a column rack. Pumps can be used to independently control the flow rates in the different zones. Columns can be arranged into 3, 4, or 5 zone arrangements. The columns are packed with polymer-based particles, uncoated silica particles, coated silica particles, or other particles suitable for the separation. The particles are typically first slurried, for example in methylene chloride, and then transferred wet into the columns. The particles are then repeatedly washed using, for example, methylene chloride. Switching times can be set using the SMB controller. The feed and desorbant are continuously pumped into the columns at room temperature. Samples of separated streams (one stream containing dihydroxy terephthalate diester in solution and another stream containing non-dihydroxy terephthalate diester containing materials) are collected from the extract port and the raffinate port over an entire switching period. The flow rates and switching time are designed to give high purity dihydroxy terephthalate diester with minimal losses of the dihydroxy terephthalate diester.

Various solvents and solvent combinations can be used to separate the dihydroxy terephthalate diester, for example BHET, from the other ingredients in the feed composition. The separation of dihydroxy terephthalate diester involves a complex interplay between several factors, including the relative solubility of the dihydroxy terephthalate diester and the other ingredients of the feed composition in various solvents, and the relative affinity of the various ingredients in the feed composition for the selected solvent(s) and packing material(s).

The solvents can be any solvent which when used in accordance with the invention enables the removal of dihydroxy terephthalate diester. In an embodiment, the solvents include one or more of water, N,N-dimethylformamide, methanol, ethanol, n-propanol, iso-propanol, n-butanol, an ether such as diethyl ether, isopropyl ether, t-butyl ether, methyl tert-butyl ether, 1,4-dioxane, oxane, and tetrahydrofuran (THF), a $C_{3-8}$ ketone such as acetone, acetonitrile, ethylene glycol, pentanes, hexanes, heptanes, octanes, and dichloromethane.

In an embodiment, the mobile phase comprises a combination of solvents. In a preferred embodiment, the mobile phase comprises an ether (for example diethyl ether, isopropyl ether, t-butyl ether, methyl tert-butyl ether, THF, 1,4-dioxane and oxane), and a hydrocarbon (for example pentanes, hexanes, heptanes, octanes, and the like). Preferably, the ether is THF and the hydrocarbon is hexanes. The relative amount of the ether and hydrocarbon can vary from greater than 0 to 100 parts ether per 100 to greater than 0 parts hydrocarbon; or 10 to 50 parts ether per 90 to 50 parts hydrocarbon. A preferred range for conducting the separation on silica is 40 to 50 parts ether per 60 to 50 parts hydrocarbon.

Alternatively, the mobile phase can contain a $C_{3-8}$ ketone such as acetone and a hydrocarbon such as hexanes. The relative amount of the ketone and hydrocarbon can vary from greater than 0 to 100 parts ketone per 100 to greater than 0 parts hydrocarbon; or 10 to 50 parts ketone per 90 to 50 parts hydrocarbon.

In another embodiment, the mobile phase can contain acetonitrile and water. The relative amount of the acetonitrile and water can vary from greater than 0 to 100 parts acetonitrile per 100 to greater than 0 parts water; or 10 to 50 parts acetonitrile per 90 to 50 parts water.

In another embodiment, the mobile phase can contain a $C_{1-4}$ alcohol and water. The relative amount of the alcohol and water can vary from greater than 0 to 100 parts alcohol per 100 to greater than 0 parts water; or 10 to 50 parts alcohol per 90 to 50 parts water.

In a preferred embodiment, simulated moving bed chromatography can be used to effectively remove BHET from feeds containing BHET and other alcoholysis products of terephthalate polyesters, specifically polyesters comprising ethylene terephthalate units on a commercial scale. More particularly, the results show that the invention is an effective method that separates at least one dihydroxy terephthalate diester-containing composition, specifically a BHET-containing composition, by liquid chromatography from a composition comprising a alcoholysis product of a composition comprising terephthalate polyesters, specifically polyesters comprising ethylene terephthalate units and at least one polymer or additive as described above.

In some embodiments, the separated dihydroxy terephthalate diester is polymerized to form a polymer product. In other embodiments, polymerizing uses at least one other comonomer with the dihydroxy terephthalate diester. Optionally, the dihydroxy terephthalate diester can be chemically reacted to produce a different monomer species.

The various embodiments are further illustrated by the following non-limiting examples.

EXAMPLES

Analytical standard samples of bis(2-hydroxyethyl) terephthalate (BHET) and bis(2-hydroxyethyl)isophthalate (BHEI) were purchased from Sigma Aldrich and Amatek Chem, respectively. Titanium (IV) isopropoxide (TPT) was purchased from Acros. All solvents were HPLC grade and purchased from Fisher Scientific. All chemicals were used without further purification. PET waste in this work was obtained from Futura Polymers. Columns were purchased from YMC, Phenomenex, Alltech, and Agilent Technologies, and more detail on column size and packing are set forth below.

General Procedure for Alcoholysis (Glycolysis) of PET

To a high pressure Parr reactor, PET flakes (62 g), ethylene glycol (94 g), and Titanium (IV) isopropoxide (TPT) (0.05 mL, 125 ppm) were added at ambient temperature. The reaction mixture was heated to 230° C. and stirred for 30-90 minutes. The crude products from the glycolysis were analyzed by HPLC.

Measurements

A high performance liquid chromatography instrument was equipped with the following: a pump capable of gradient elution, solvent degasser, thermostatted column compartment, different columns from various vendors as shown in Table 1 and 2, UV detector capable of monitoring 260 and 280 nm, and Chemstation (or similar data analysis software).

TABLE 1

Summary of HPLC/UV method and instrument parameters.

| Column | Eclipse XBD-C18 5 μm, 150 mm × 4.6 mm (Agilent Technologies) | | |
|---|---|---|---|
| Column temperature | 25° C. | | |
| Wavelength | 260, 280 nm | | |
| Mobile phase A | water | | |
| Mobile phase B | acetonitrile | | |
| Mobile phase C | methanol | | |
| Injection Volume | 5 μL | | |
| Flow rate | 1.0 mL/min | | |
| Gradient Time (min) | Mobile phase A | Mobile phase B | Mobile phase C |
| 0 | 90 | 9 | 1 |
| 12 | 50 | 45 | 5 |
| 20 | 0 | 90 | 10 |
| 28 | 0 | 100 | 0 |
| 24 | 0 | 100 | 0 |

TABLE 2

Different columns from various vendors.

| Vendor | Column | Size |
| --- | --- | --- |
| YMC | Diol-NP HG, 120 A | 50 μm, 100 mm × 10 mm |
| Phenomenex | Luna 5μ NH2, 100 A | 5 μm, 150 × 4.6 mm |
| Phenomenex | Luna 5μ HILIC, 200 A | 5 μm, 150 × 4.6 mm |
| Phenomenex | Luna 5μ CN, 100 A | 5 μm, 100 × 4.6 mm |
| Phenomenex | TSKgel 5μ Amide-80 | 5 μm, 250 × 4.6 mm |
| Alltech | Inertsil Silica 5μ | 5 μm, 150 × 4.6 mm |

Sample Preparation Procedure

Each HPLC sample was prepared by weighing 500 mg of crude BHET in a volumetric flask and adding appropriate solvents to adjust the volume to 100 mL.

Solubility of BHET in Different Solvents 10 ml of the designated solvent was added to a scintillation vial with 2 g of BHET. The vial was placed in a shaker, shaken for 2 hours and the contents were analyzed by HPLC.

Glycolysis of Waste PET

In order to identify the structure of the main product in the depolymerization of PET by ethylene glycol catalyzed by TPT, various characterizations, such as GC-MS, NMR, and HPLC were performed. The HPLC chromatogram showed that the main product was BHET at 7.4 minutes, which compared well with the standard BHET purchased from Sigma Aldrich. The major impurity from the glycolysis was O,O'-ethane-1,2-diylbis(2-hydroxyethyl) diterephthalate, the dimer of BHET, with the retention time of 13.2 minutes. The GC-MS spectrum showed another byproduct from the glycolysis of PET to be 2-(2-hydroxyethoxyl)ethyl (2-hydroxyethyl) terephthalate, structure provided below, at the retention time of 8.0 minutes.

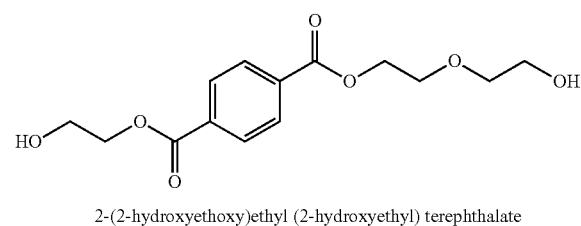 [SMILES: O=C(OCCO)c1ccc(C(=O)OCCOCCO)cc1]

2-(2-hydroxyethoxy)ethyl (2-hydroxyethyl) terephthalate

A study of the effect of reaction times on the percent conversion of glycolysis was performed and appears in Table 3. The results indicated that there was very little variance in the percent conversion over the reaction times of 30, 45, 60, and 90 minutes.

TABLE 3

Study of reaction times and percent conversion of BHET in glycolysis of PET.

| Entry | Time (min) | % BHET | Dimer of BHET |
| --- | --- | --- | --- |
| 1 | 30 | 75 | 17 |
| 2 | 45 | 75 | 18 |
| 3 | 60 | 75 | 17 |
| 4 | 90 | 74 | 15 |

Example 1

Separation of BHET by n-Propanol and Water

The crude product was dissolved in n-propanol and loaded onto an Eclipse XBD-C18 column (150 mm×4.6 mm) from Agilent, pre-equilibrated with chosen conditions i.e. 2, 4, 6, 8, 10, and 12% of n-propanol in water at a flow rate of 1.0 mL/min. The column was eluted with the same designated conditions, and the elution was monitored by measuring the absorbance at 260 and 280 nm. The results from HPLC showed that with 2-4% of n-propanol/water all the chemicals remained in the column. When increasing % n-propanol to 6%, BHET and impurity 1 eluted from the column with the retention times of 9.47 and 11.53, respectively. Increasing the % n-propanol resulted in a shortening of the retention times for BHET and other impurities. The HPLC chromatograms of the crude product with different conditions and the retention times of BHET and impurities are summarized in Table 4.

TABLE 4

Observed retention times ($t_R$) of BHET and other impurities.

| Entry | % n-propanol/Water | BHET ($t_R$) | Impurity 1 ($t_R$) | Impurity 2 ($t_R$) | Impurity 3 ($t_R$) |
| --- | --- | --- | --- | --- | --- |
| 1 | 2 | nd[a] | nd[a] | nd[a] | nd[a] |
| 2 | 4 | nd[a] | nd[a] | nd[a] | nd[a] |
| 3 | 6 | 9.47 | 11.53 | nd[a] | nd[a] |
| 4 | 8 | 5.96 | 7.30 | nd[a] | nd[a] |
| 5 | 10 | 4.54 | 5.13 | 20.25 | nd[a] |
| 6 | 12 | 3.57 | M[b] | 11.17 | 16.09 |

[a] Not detectable, i.e., the chemicals remained in the column.
[b] Impurity 1 mixed with BHET.

Example 2

Separation of BHET by Ethanol and Water

The crude product was dissolved in ethanol and loaded onto an Eclipse XBD-C18 column (150 mm×4.6 mm) from Agilent, pre-equilibrated with chosen conditions, i.e., 2, 4, 6, 8, 10, 12, 14, and 16% of ethanol in water at a flow rate of 1.0 mL/min. The column was eluted with the same designated conditions, and the elution was monitored by measuring the absorbance at 260 and 280 nm. The results from HPLC showed that with 2-8% of ethanol/water all the chemicals remained in the column. When increasing the % ethanol to 10%, BHET and impurity 1 eluted from the column with the retention times of 20.39 and 24.42, respectively. Increasing the % ethanol resulted in a shortening of the retention times for BHET and other impurities. The retention times of BHET and impurities are summarized in Table 5.

TABLE 5

Observed retention times ($t_R$) of BHET and other impurities.

| Entry | % Ethanol/Water | BHET ($t_R$) | Impurity 1 ($t_R$) | Impurity 2 ($t_R$) | Impurity 3 ($t_R$) |
| --- | --- | --- | --- | --- | --- |
| 1 | 2-8 | nd[a] | nd[a] | nd[a] | nd[a] |
| 2 | 10 | 20.39 | 24.42 | nd[a] | nd[a] |
| 3 | 12 | 9.83 | 11.54 | 33.39 | nd[a] |
| 4 | 14 | 6.18 | 6.73 | 18.39 | 33.01 |
| 5 | 16 | 4.77 | M[b] | 10.33 | 13.57 |

[a] Not detectable, i.e., the chemicals remained in the column.
[b] Impurity 1 mixed with BHET.

Example 3

Separation of BHET by Methanol and Water

The crude product was dissolved in methanol and loaded onto an Eclipse XBD-C18 column (150 mm×4.6 mm) from Agilent, pre-equilibrated with chosen conditions, i.e., 22, 24, 26, 30, and 34% of methanol in water at a flow rate of 1.0 mL/min. The column was eluted with the same designated conditions, and the elution was monitored by measuring the absorbance at 260 and 280 nm. The results from HPLC showed that with 22% of methanol/water only BHET eluted out of the column with a retention time of 22.35, and the other impurities remained in the column. When increasing the % methanol to 24%, BHET and impurity 1 eluted from the column with retention times of 16.97 and 27.23 respectively. When the % methanol was increased, the retention times of BHET and other impurities were shortened. The retention times for BHET and impurities are shown in Table 6.

TABLE 6

Observed retention times ($t_R$) of BHET and other impurities.

| Entry | % Methanol/Water | BHET ($t_R$) | Impurity 1 ($t_R$) | Impurity 2 ($t_R$) | Impurity 3 ($t_R$) |
|---|---|---|---|---|---|
| 1 | 22 | 22.35 | nd$^a$ | nd$^a$ | nd$^a$ |
| 2 | 24 | 16.97 | 27.23 | nd$^a$ | nd$^a$ |
| 3 | 26 | 13.81 | 21.47 | nd$^a$ | nd$^a$ |
| 4 | 30 | 9.43 | 13.70 | nd$^a$ | nd$^a$ |
| 5 | 34 | 6.66 | 8.99 | 29.52 | nd$^a$ |

$^a$Not detectable, i.e., the chemicals remained in the column.

Example 4

Separation of BHET by Acetonitrile and Water

The crude product was dissolved in acetonitrile and loaded onto an Eclipse XBD-C18 column (150 mm×4.6 mm) from Agilent, pre-equilibrated with chosen conditions i.e. 10, 12, 14, 16, and 18% of acetonitrile in water at a flow rate of 1.0 mL/min. The column was eluted with the same designated conditions, and the elution was monitored by measuring the absorbance at 260 and 280 nm. The results from HPLC showed that with 10% of acetonitrile/water, only BHET eluted from the column with a retention time of 26.41, and the other impurities remained in the column. When increasing the % acetonitrile to 12%, BHET and impurity 1 eluted out from the column with retention times of 16.13 and 25.66, respectively. The same trend was observed when the % acetonitrile was increased, the retention times of BHET and other impurities were decreased. The retention times for BHET and impurities are summarized in Table 7.

TABLE 7

Observed retention times ($t_R$) of BHET and other impurities.

| Entry | % Acetonitrile/Water | BHET ($t_R$) | Impurity 1 ($t_R$) | Impurity 2 ($t_R$) | Impurity 3 ($t_R$) |
|---|---|---|---|---|---|
| 1 | 10 | 26.41 | nd$^a$ | nd$^a$ | nd$^a$ |
| 2 | 12 | 16.13 | 25.66 | nd$^a$ | nd$^a$ |
| 3 | 14 | 10.59 | 15.54 | nd$^a$ | nd$^a$ |
| 4 | 16 | 7.47 | 10.23 | nd$^a$ | nd$^a$ |
| 5 | 18 | 5.62 | 7.19 | 22.78 | nd$^a$ |

$^a$Not detectable, i.e., the chemicals remained in the column.

Table 8 summarizes the retention times of different solvent conditions that can separate BHET from the impurities using the C18 column. Although the conditions reported here can be used to isolate BHET, the solubility of BHET in conditions with a high percentage of water presents a limitation for scaling the process up to SMB Chromatography due to limited solubility of BHET in water (0.5% (w/v)). As a result, when a high percentage of water is present, a large amount of solvent is required for SMB Chromatography, reducing the economic viability of the process.

TABLE 8

Summary of retention times of different solvent conditions for separation of BHET.

| Entry | % Solvent/Water | BHET ($t_R$) | Impurity 1 ($t_R$) | Impurity 2 ($t_R$) | Impurity 3 ($t_R$) |
|---|---|---|---|---|---|
| 1 | 6 (n-propanol) | 9.47 | 11.53 | nd$^a$ | nd$^a$ |
| 2 | 12 (ethanol) | 9.83 | 11.54 | nd$^a$ | nd$^a$ |
| 3 | 30 (methanol) | 9.43 | 13.70 | nd$^a$ | nd$^a$ |
| 4 | 14 (acetonitrile) | 10.59 | 15.54 | nd$^a$ | nd$^a$ |

$^a$Not detectable, i.e., the chemicals remained in the column.

TABLE 9

Solubility of BHET in different solvents (% w/v).

| Entry | Solvent | % Solubility (w/v) |
|---|---|---|
| 1 | Dichloromethane | 1.12 |
| 2 | ethylene glycol | 2.81 |
| 3 | Acetonitrile | 4.98 |
| 4 | iso-propanol | 6.16 |
| 5 | Ethanol | 8.61 |
| 6 | Acetone | 9.09 |
| 7 | THF | 12.60 |
| 8 | Methanol | 13.75 |
| 9 | DMF | 60 |
| 10 | hexanes | ~0 |

In order to address the low % loading of BHET, alternative solvents were evaluated. The solubility of BHET in different organic solvents appears in Table 9. The objective was to find appropriate solvent conditions with a % loading of BHET usually 5% (w/v), and to find suitable adsorbents for BHET purification. The results indicated that DMF was a good solvent to dissolve BHET (60% (w/v)) and which addresses the solubility problem. However, since DMF has a high boiling point as well as high viscosity, DMF would be expected to be problematic in SMB chromatography due to the energy cost required to recover the high boiling point solvent and the high pressure which would need to generated in the column due to the high viscosity of DMF. Other alternative solvents that were examined to address the low % loading are methanol, acetone, and THF with BHET solubilities of 13.75, 9.09, and 12.60% (w/v), respectively. Different adsorbents were purchased from various vendors. The type of columns and sizes are shown in Table 3.

Examples 5 and 6, Comparative Examples A to C

HPLC Separation of Crude BHET with Different Columns

Column packed with Diol-NP was first evaluated and the results indicated that 4% MeOH/DCM (Ex. 5a), 8% MeOH/DCM (Ex. 5b), 15% ACN/DCM (Ex. 5c), and 5% iso-propy alcohol/DCM (Ex. 5d) can separate BHET from the impurities. However, the low % loading still was not solved using these conditions with the Diol-NP column. When Luna 5μ NH2 (Comp. Ex. A1), Luna 5μ HILIC (Comp. Ex. A2), TSK-gel 5μ Amide-80 (Comp. Ex. A3), and Inertsil Silica 5μ (Comp. Ex. A4) were evaluated under 0-100% MeOH/DCM, there was no separation of BHET from the impurities. The eluent of 0-100% THF/DCM was also studied (Comp. Ex. B).

The HPLC results indicated no sign of good separation of BHET from the impurities similar to what was observed from 0-100% MeOH/DCM. When 0-100% THF/Hexanes was screened with Luna 5μ NH2 (Comp. Ex. C1), Luna 5μ HILIC (Comp. Ex. C2), TSKgel 5μ Amide-80 (Comp. Ex. C3), and Inertsil Silica 5μ (Ex. 6), it was surprisingly found that 45% THF/Hexanes with Inertsil Silica showed a promising separation of BHET ($t_R$=15.12) from the impurities as seen by the HPLC chromatogram. In order to confirm the purity of BHET obtained from this condition, fractionation of certain peaks were analyzed by HPLC and GC-MS. The result showed that the peak in the range of 14.5-18.5 minutes had a purity of 99.9%. With 12.6% solubility of BHET in THF, the solubility of BHET in 45% THF/Hexanes was estimated to be 5.67%. Therefore, the Inertsil Silica column with 45% THF/Hexanes performed surprisingly well for purifying crude BHET from glycolysis of PET.

Example 7

Separation of BHET with THF/Hexanes

Surprisingly good results were obtained with the HPLC method using an isocratic solution (45% THF/Hexanes) with Inertsil Silica 5μ (5 μm, 150×4 6 mm) column for the separation of crude BHET from the glycolysis product of Futura grade PET flakes. The purity of BHET obtained from this method was found to be 99.9%.

A simulated moving bed process based upon this surprisingly effective combination is provided. In SMBC the solid phase in this particular case, silica, comprises individual columns connected in series, and the mobile phase (45% THF/hexanes) by inlet streams of Feed (Sample in 45% THF/hexanes) and Desorbent (45% THF/hexanes) and outlet streams of raffinate (waste) and extract (BHET). Valves between the columns are systematically switched open or closed at timed intervals to introduce the inlet streams and withdraw the outlet streams between the separation zones. By adjusting the stream flow rates, the switch time, and the Desorbent composition accordingly, a cycle will be established wherein Feed and Desorbent are simultaneously added and highly purified BHET are continuously recovered.

Separation of BHET by THF and Hexane with a Luna 100 A CN Column

The crude product was dissolved in acetonitrile and loaded onto a Luna 100A CN (50 mm×4.6 mm) from Phenomenox, pre-equilibrated with chosen conditions i.e. 15, 20, 25, 30, 35, and 45% of THF in hexanes at a flow rate of 1.0 mL/min. The column was eluted with the same designated conditions, and the elution was monitored by measuring the absorbance at 260 nm. The results from HPLC showed that with 15% of THF/hexanes, only BHET and impurity 1 eluted from the column with a retention time of 9.063 and 11.096, and the other impurities remained in the column. When increasing the % THF to 20%, BHET and impurity 1 eluted out from the column with retention times of 5.146 and 6.082 respectively along with other impurity 3 and 4 at 8.28 and 14.07. When the % THF was further increased, the retention times of BHET and other impurities decreased. Further, we observed the overlapping of retention times of BHET with impurities. At 45%, we observed no separation between BHET and impurities. The retention times for BHET and impurities are summarized in Table 10.

TABLE 10

Observed retention times ($t_R$) of BHET and other impurities.

| Entry | % THF/ Hexanes | BHET ($t_R$) | Impurity 1 ($t_R$) | Impurity 2 ($t_R$) | Impurity 3 ($t_R$) | Impurity 4 ($t_R$) |
|---|---|---|---|---|---|---|
| 1 | 15 | 9.063 | 11.096 | nd[a] | nd[a] | nd[a] |
| 2 | 20 | 5.146 | 6.082 | 8.281 | 14.074 | nd[a] |
| 3 | 25 | 3.465 | 3.920 | 4.775 | 5.464 | 6.67 |
| 4 | 30 | 2.702 | 2.964 | 3.327 | 3.671 | 4.182 |
| 5 | 35 | 2.189 | nd[a] | 2.472 | nd[a] | 2.832 |
| 6 | 45 | 1.726 | nd[a] | nd[a] | nd[a] | nd[a] |

[a]Not detectable, i.e., either overlapping with other impurities or beyond the measurement time.

The experiments were repeated at 30% THF concentration for post manufacturing and post-consumer used materials also gave encouraging results (Table 11).

TABLE 11

Observed retention times ($t_R$) of BHET and other impurities for PET post manufacturing and post-consumer use

| Entry | BHET ($t_R$) | Impurity 1 ($t_R$) | Impurity 2 ($t_R$) | Impurity 3 ($t_R$) | Impurity 4 ($t_R$) |
|---|---|---|---|---|---|
| BHET Flakes | 2.564 | 2.792 | 3.1 | 3.83 | 4.92 |
| Chopped Fiber | 2.557 | 2.792 | 3.1 | 3.83 | 4.987 |
| PET fiber | 2.559 | 2.796 | 3.11 | 3.849 | |
| PET fines | 2.557 | 2.782 | 3.1 | 3.83 | 4.791 |
| PET Lump | 2.55 | 2.769 | 3.087 | 3.802 | |
| PET yarn | 2.575 | 2.805 | 3.12 | 3.823 | 4.896 |
| Seat Belt | 2.554 | 2.785 | 3.098 | 3.829 | 4.987 |

Example 8

Separation of BHET by Acetone and Hexanes

The crude product was dissolved in acetonitrile and loaded onto a Luna 100A CN (50 mm×4.6 mm) from Phenomenox, pre-equilibrated with chosen conditions i.e. 25, 30, 35 of acetone in Hexanes at a flow rate of 1.0 mL/min. The column was eluted with the same designated conditions, and the elution was monitored by measuring the absorbance at 218 nm (IR radiation). The results from HPLC showed that with 10% of acetonitrile/water, only BHET eluted from the column with a retention time of 26.41, and the other impurities remained in the column. When increasing the % acetone to 25%, BHET and impurity 1 eluted out from the column with retention times of 2.9 and 3.134 respectively. When the % acetonitrile was further increased the retention times of BHET overlapped with impurity 1, further, we also observed a decrease in the retention time. The retention times for BHET and impurities are summarized in Table 12.

TABLE 12

Observed retention times ($t_R$) of BHET and other impurities.

| Entry | % Acetone/ Hexanes | BHET ($t_R$) | Impurity 1 ($t_R$) | Impurity 2 ($t_R$) | Impurity 3 ($t_R$) | Impurity 4 ($t_R$) |
|---|---|---|---|---|---|---|
| 1 | 25 | 2.9 | 3.134 | 3.510 | 3.807 | 4.314 |
| 2 | 30 | 2.354 | nd[a] | 2.659 | nd[a] | 3.006 |
| 3 | 35 | 2.015 | nd[a] | 2.152 | nd[a] | 2.337 |

[a]Not detectable, i.e., the chemicals remained in the column.

As used herein, the singular forms "a," "an," and "the" include plural referents unless the context clearly dictates otherwise. "Or" means "and/or." All quantities are to be understood as being modified by "about," which is inclusive of the stated value and has the meaning dictated by the context (e.g., includes the degree of error associated with measurement of the particular quantity).

The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.).

As used herein, a "combination" is inclusive of blends, mixtures, alloys, reaction products, and the like.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

All references cited herein are incorporated by reference in their entirety.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

We claim:

1. A method of recycling a bis(hydroxyalkyl) terephthalate monomer from a composition comprising a terephthalate-containing polymer, the method comprising:
    depolymerizing the terephthalate-containing polymer to provide the bis(hydroxyalkyl) terephthalate; and
    separating the bis(hydroxyalkyl) terephthalate from the composition comprising the depolymerized terephthalate-containing polymer by continuous multi-column liquid chromatography.

2. The method of claim 1, wherein the depolymerizing comprises alcoholysis of the terephthalate-containing polymer.

3. The method of claim 2, further comprising hydrolysis of the terephthalate-containing polymer composition.

4. The method of claim 1, wherein the separating comprises use of a mobile phase comprising a combination of solvents.

5. The method of claim 4, wherein the mobile phase comprises an ether and a hydrocarbon.

6. The method of claim 5, wherein the ether is tetrahydrofuran and the hydrocarbon is hexanes.

7. The method of claim 4, wherein the mobile phase comprises a $C_{3-8}$ ketone and a hydrocarbon.

8. The method of claim 7, wherein the ketone is acetone and the hydrocarbon is hexanes.

9. The method of claim 4, wherein the mobile phase comprises acetonitrile and water.

10. The method of claim 4, wherein the mobile phase comprises a $C_{1-4}$ alcohol and water.

11. The method of claim 1, wherein the separating comprises use of a stationary phase comprising silica.

12. The method of claim 11, wherein the silica is a functionalized silica gel.

13. The method of claim 1, further comprising polymerizing the bis(hydroxyalkyl) terephthalate to form a polymer product.

14. The method of claim 13, wherein polymerizing is in the presence of at least one other comonomer with the bis(hydroxyalkyl) terephthalate.

15. The method of claim 1, further comprising chemically reacting the bis(hydroxyalkyl) terephthalate to produce a different monomer species.

16. The method of claim 15, further comprising polymerizing the different monomer species to form a polymer product.

17. The method of claim 15, wherein the polymerizing the different monomer species is in the presence of at least one other comonomer with the different monomer species.

18. A method of recycling a polyester comprising ethylene terephthalate units, the method comprising:
    depolymerizing the polyester in the presence of a $C_{1-5}$ alkylene diol and an alcoholysis catalyst to provide a composition comprising bis(hydroxyalkyl) terephthalate; and
    separating the bis(hydroxyalkyl) terephthalate from the depolymerized composition by continuous multi-column liquid chromatography, using a silica stationary phase and a mobile phase composition comprising a combination of solvents.

19. The method of claim 18, wherein the mobile phase comprises an ether and a hydrocarbon.

20. The method of claim 19, wherein the ether is tetrahydrofuran and the hydrocarbon is hexanes.

21. The method of claim 18, wherein the mobile phase comprises a $C_{3-8}$ ketone and a hydrocarbon.

22. The method of claim 21, wherein the ketone is acetone and the hydrocarbon is hexanes.

23. The method of claim 18, wherein the mobile phase comprises acetonitrile and water.

24. The method of claim 18, wherein the mobile phase comprises a $C_{1-4}$ alcohol and water.

25. The method of claim 18, wherein the silica is a functionalized silica gel.

26. The method of claim 18, further comprising polymerizing the bis(hydroxyalkyl) terephthalate to form a polymer product.

27. The method of claim 26, wherein polymerizing comprises use of at least one other comonomer with the bis(hydroxyalkyl) terephthalate.

28. The method of claim 18, further comprising chemically reacting bis(hydroxyalkyl) terephthalate to produce a different monomer species.

29. The method of claim 18, further comprising polymerizing the different monomer species to form a polymer product.

30. The method of claim 29, wherein polymerizing the different monomer species comprises use of at least one other comonomer with the different monomer species.

31. A method of recycling a polyester comprising ethylene terephthalate units, the method comprising:
    depolymerizing the polyester in the presence of ethylene glycol and a glycolysis catalyst to provide a composition comprising bis(2-hydroxyethyl) terephthalate; and
    separating the bis(2-hydroxyethyl) terephthalate from the depolymerized composition by continuous multi-column liquid chromatography, using a silica stationary phase and a mobile phase composition comprising a combination of solvents.

32. The method of claim 31, wherein the silica gel composition is a functionalized silica gel.

33. The method of claim 31, wherein the mobile phase comprises an ether and a hydrocarbon.

34. The method of claim 33, wherein the ether is tetrahydrofuran and the hydrocarbon is hexanes.

35. The method of claim 31, wherein the mobile phase comprises a $C_{3-8}$ ketone and a hydrocarbon.

36. The method of claim 35, wherein the ketone is acetone and the hydrocarbon is hexanes.

37. The method of claim 31, wherein the mobile phase comprises acetonitrile and water.

38. The method of claim 31, wherein the mobile phase comprises a $C_{1-4}$ alcohol and water.

39. The method of claim 31, further comprising polymerizing the bis(2-hydroxyethyl) terephthalate to form a polymer product.

40. The method of claim 39, wherein polymerizing comprises use of at least one other comonomer with the bis(2-hydroxyethyl) terephthalate.

41. The method of claim 31, further comprising chemically reacting bis(2-hydroxyethyl) terephthalate to produce a different monomer species.

42. The method of claim 41, further comprising polymerizing the different monomer species to form a polymer product.

43. The method of claim 42, wherein polymerizing the different monomer species comprises use of at least one other comonomer with the different monomer species.

\* \* \* \* \*